United States Patent
Tuohey et al.

(10) Patent No.: US 9,969,965 B2
(45) Date of Patent: May 15, 2018

(54) LINEARLY SCALABLE SINGLE USE BIOREACTOR SYSTEM

(75) Inventors: Colin Tuohey, Medway, MA (US); Ted Deloggio, Allentown, PA (US); Thomas Erdenberger, Arlington, MA (US); Kenneth P. Clapp, Marlborough, MA (US); Richard Damren, Marlborough, MA (US); Parrish M. Galliher, Littleton, MA (US); Patrick Guertin, Mendon, MA (US); Jiyoung Lee, New York, NY (US); Michael Fisher, Ashland, MA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 0 days. days.

(21) Appl. No.: 13/978,726

(22) PCT Filed: Jan. 11, 2012

(86) PCT No.: PCT/US2012/020963
§ 371 (c)(1),
(2), (4) Date: Jul. 9, 2013

(87) PCT Pub. No.: WO2012/097079
PCT Pub. Date: Jul. 19, 2012

(65) Prior Publication Data
US 2013/0288346 A1    Oct. 31, 2013

Related U.S. Application Data (60) Provisional application No. 61/431,798, filed on Jan. 11, 2011.

(51) Int. Cl.
*C12M 1/00*    (2006.01)
*C12N 1/06*    (2006.01)
*C12M 1/06*    (2006.01)

(52) U.S. Cl.
CPC .......... *C12M 23/28* (2013.01); *C12M 23/02* (2013.01); *C12M 23/14* (2013.01); *C12M 23/26* (2013.01); *C12M 27/02* (2013.01)

(58) Field of Classification Search
CPC ....... C12M 23/26; C12M 23/28; C12M 27/02
(Continued)

(56) References Cited

U.S. PATENT DOCUMENTS 7,629,167 B2    12/2009    Hodge et al.
2003/0129659 A1*    7/2003    Whelihan et al. ............. 435/7.1
(Continued)

FOREIGN PATENT DOCUMENTS

CN    102307984    1/2012
EP    2216395 A1    8/2010
(Continued)

OTHER PUBLICATIONS

Kehoe et al., Scalable Stirred-Suspension Bioreactor Culture of Human Pluripotent Stem Cells, Tissue Engineering: Part A, vol. 16, No. 2, (2010).*
(Continued)

*Primary Examiner* — Gautam Prakash
(74) *Attorney, Agent, or Firm* — Grogan, Tuccillo & Vanderleeden, LLP (57) ABSTRACT

Disclosed is a single-use bioreactor bag design providing substantially equivalent maximum shear rate at the impeller tip and average or bulk shear rate over a range of power per unit working volume and rpm needed for bioculture processing. The uniformity in shear profile of the bag design providing a unique advantage when used as a scale-down or scale-up platform. Also disclosed is a linearly scalable, single-use, bioreactor system for use in carrying out a scalable biomanufacturing process, the system comprising two single-use bioreactor bags of different volumes, wherein
(Continued)

the ratio H/D of the height of the working volume H to the diameter D of the tank, or of the bag is equal to about 1.5, and the bulk shear in each of the bags is substantially constant. The disclosed small scale system models larger scale systems from both a shear/scalability/performance basis and also from a validation and regulatory basis. In summary, the 10L bioreactor system disclosed provides for "linear scalability" by using the same or substantially simulating the same vessel geometry, gas sparging system, impeller shape and type, polymer composition of the flexible bag/components, process control system, and shear rates as larger 50-5000 L systems.

13 Claims, 2 Drawing Sheets

(58) Field of Classification Search
USPC .................................................... 435/287.1
See application file for complete search history.

(56) References Cited

U.S. PATENT DOCUMENTS

| | | | |
|---|---|---|---|
| 2005/0158701 A1* | 7/2005 | West | 435/286.1 |
| 2005/0239199 A1* | 10/2005 | Kunas et al. | 435/297.1 |
| 2008/0068920 A1 | 3/2008 | Galliher et al. | |
| 2008/0131957 A1 | 6/2008 | Ryan et al. | |
| 2009/0180933 A1* | 7/2009 | Kauling et al. | B01F 3/04269 422/82.08 |
| 2009/0188211 A1* | 7/2009 | Galliher et al. | 435/287.1 |
| 2009/0290962 A1 | 11/2009 | Fisher et al. | |

FOREIGN PATENT DOCUMENTS

| | | |
|---|---|---|
| WO | WO 2010/089151 | 8/2010 |
| WO | 2010139470 A1 | 12/2010 |
| WO | WO 2010/139470 | 12/2010 |

OTHER PUBLICATIONS

Search Report dated Apr. 14, 2014 Issued on Corresponding Chinese Patent Application No. 201280005013.7.
Ding, X., et al., Liquid Agitation, 1983, English translation of relevant pages.
Wang, X., et al., Principles of Chemical Industry, 2009, English translation of relevant pages.
Wu, et al., Estimation of Agitator Flow Shear Rate. Wiley InterScience, Apr. 7, 2006.
Perez, et al., Chemical Engineering Journal, 124:1-5, 2006.
European Search Report dated May 4, 2017 on Corresponding Application No. 12733903.4-1501/2663629 PCT/US2012020963.

* cited by examiner

FIG. 1

LINEARLY SCALABLE SINGLE USE BIOREACTOR SYSTEM

CROSS-REFERENCE TO RELATED APPLICATIONS

This application is a filing under 35 U.S.C. 371 of international application number PCT/US2012/020963, filed Jan. 11, 2012, published on Jul. 19, 2012 as WO 2012/097079, which claims priority to U.S. provisional patent application No. 61/431,798 filed Jan. 11, 2011.

FIELD OF INVENTION

The present disclosure relates to bioreactor systems and methods for processing biological materials. In some embodiments, the disclosed bioreactor systems include disposable components.

BACKGROUND

Cell culturing is an essential step in manufacturing biological products.

Mammalian cells, for example, Chinese hamster ovary (CHO) cells, are often cultured in order to produce therapeutic proteins. Such proteins may include, e.g., monoclonal antibodies (MAbs), erythropoietin (EPO), and interferons. Mammalian cells are also cultured to produce nucleic acids, viruses for use in vaccines, and antibodies. Microbial cells, e.g., bacteria or yeast, are also used for recombinant protein production for use in pharmaceuticals.

In scaling up cultures from the laboratory bench-top bioreactor to larger commercial production bioreactors, it is important to consider some differences in the requirements of mammalian cells and microbial cells, or microbes. In contrast to microbial cells, e.g., mammalian cells lack a tough outer wall. Mammalian cells typically have a diameter of about 10 micrometers (10 μm), whereas most microbial cells are typically only 1 micrometer (1 μm) or less in diameter. The larger size and the lack of a tough outer wall make mammalian cells much more shear-sensitive and fragile than are microbial cells. It is important to ensure that the materials in the bioreactor are adequately and evenly dispersed within a reasonable time period. In order to minimize shearing and protect the fragile cells, bioreactors designed for culturing mammalian cells have impellers that gently mix the cell culture suspension or the suspension of microcarriers with attached cells. In the biotech/pharmaceutical manufacturing industry, "technical transfer," also referred to as "technology transfer" (hereinafter, "tech transfer") of a biopharmaceutical process, such as, e.g., cell culturing, from the research or development level, i.e., small-scale production, to large scale, commercial production is generally a complex, costly, and time consuming process.

Difficulties in the tech transfer process are often encountered because the development level process may include many degrees of freedom, whereas the large scale process may require strictly controlled parameters. A small scale process may work well in the laboratory, but may not work well in a larger volume, or scaled-up process. Often a complete process redesign is required upon tech transfer from a small scale volume to a single, larger scale volume. Further, the small scale process may have been developed without using equipment certified for current good manufacturing practices (cGMP) that are essential for commercial production.

Thus, there is an on-going need in biopharmaceutical development and manufacturing for an easily scalable system and process that provide an easy, reliable, and repeatable tech transfer to large scale production with robustness and cGMP compliance, and without the need for substantial re-testing and further development and refinement of the process. The tech transfer often includes the process protocols, documentation, data, stability data, and training in the techniques used in small scale. However, there is often an urgent need for extensive, time-consuming modifications in the small scale protocol in order to achieve a useable protocol for robust, larger scale production processes and systems.

BRIEF SUMMARY OF THE DISCLOSURE

The inventors of the present subject matter have now discovered a linearly scalable, single-use bioreactor system and method for carrying out a scalable mammalian cell biomanufacturing process that solves many of the recognized problems in modeling and scaling up the process for commercial production. Use of the disclosed system and method minimizes risks and helps ensure that the robustness, purity, and potency of the scaled-up process are comparable to that of the small-scale development process. Tech transfer using the disclosed system can provide optimal results, and a safe and cGMP compliant scaled up process for manufacturing, while eliminating the need for costly and time-consuming process redesign. In summary, the 10 L bioreactor system disclosed provides for "linear scalability" by using the same, or substantially simulating the same, vessel geometry, gas sparging system, impeller shape and type, polymer composition of the flexible bag/components, process control system, and shear rates as in the larger 50 liter through 5000 liter systems. The invention, inter alia, includes the following, alone or in combination.

In one aspect, the present invention relates to a linearly scalable bioreactor system for use in carrying out a scalable biomanufacturing process, the system comprising: a bioprocessing bag having a flexible wall, a working volume of from about 2 liters to about 10 liters, and a height to diameter ratio at maximum working volume of about 1.5; an impeller mounted on an impeller plate attached to an inside bottom surface of the flexible wall, the ratio of the diameter of the impeller, Di, to the diameter of the bioprocessing bag, Dt, equal to a value of from about 0.6 to about 0.7, the bioprocessing bag capable of exhibiting substantially the same impeller shear rate and bulk shear rate over a range of values of power per unit volume.

In another aspect, the present invention relates to a linearly scalable bioreactor system for use in carrying out a scalable biomanufacturing process, the system comprising: a first bioprocessing bag having a first volume, a first flexible wall, and an aspect ratio of first bag height at the first bag maximum working volume to first bag diameter equal to a first H/D; a first impeller mounted on a first impeller plate attached to a first inside surface of the first flexible wall, the ratio of the first impeller, Di, to the diameter of the first bioprocessing bag, Dt, equal to a value of from about 0.6 to about 0.7; a second bioprocessing bag having a second volume that is larger than the first volume of the first bioprocessing bag, a second flexible wall, and an aspect ratio of second bag height at the second bag maximum working volume to second bag diameter equal to a second H/D, wherein the first and the second H/D are substantially equal to one another; a second impeller mounted on a second impeller plate attached to a second inside surface of the second flexible wall, the ratio of the diameter of the second impeller, D2i, to the diameter of the second bioprocessing bag, D2t, is deliberately not equal to a value of from about 0.6 to about 0.7; and wherein the first and the second impeller are of the same type, and are each positioned over a sparging surface and are each configured to operate within the first and second bag, respectively, such that, in a bioprocessing operation utilizing the same fluid within the first and the second bioprocessing bags, under similar conditions, and at the same power per unit volume, the average or bulk shear rate value of the fluid in the first bioprocessing bag is within +/−25 percent of the average or bulk shear rate value of the fluid in the second bioprocessing bag.

Another embodiment of the invention is a linearly scalable 10 liter bioprocessing system which substantially simulates the shear and power/unit volume characteristics of any one of a 50 liter to a 5000 liter bioprocessing system comprising a flexible-walled bioreactor bag, the 10 liter bioprocessing system comprising:
a bioprocessing bag having a working volume of from about 2 liters to about 10 liters; a flexible wall; and an impeller mounted on an impeller plate attached to an inside bottom surface of the flexible wall, the ratio of the diameter of the impeller, Di, to the diameter of the bioprocessing bag, Dt, equal to a value of from about 0.6 to about 0.7, the bioprocessing bag capable of exhibiting substantially the same impeller shear rate and bulk shear rate over a range of values of power per unit volume.

In another aspect, the present invention relates to a linearly scalable 10 liter bioprocessing system having a bioreactor process control system that uses the same, or substantially simulates a process control system of any one of a 50 liter to a 5000 liter bioprocessing system comprising a flexible-walled bioreactor bag, the 10 liter bioprocessing system comprising: a bioprocessing bag having a working volume of from about 2 liters to about 10 liters; a flexible wall; an impeller mounted on an impeller plate attached to an inside bottom surface of the flexible wall, the ratio of the diameter of the impeller, Di, to the diameter of the bioprocessing bag, Dt, equal to a value of from about 0.6 to about 0.7, the bioprocessing bag capable of exhibiting substantially the same impeller shear rate and bulk shear rate over a range of values of power per unit volume; a process measuring system; a system of field actuating devices or field actuators; and a local processing unit and associated software logic configured to convert a measuring system input and pass the measuring system input to a supervisory controller or human machine input device for data manipulation and storage and to transform the measuring system input from the supervisory controller or human machine input device to a manipulation of the field actuating device or the field actuator.

The linearly scalable 10 liter bioprocessing system having a ten liter bioreactor process control system as described above may have a human machine interface and associated software programming comprising at least one of a computer mouse, a keyboard and a touch-screen; and a supervisory controller and software programming capable of acting on a specific configurable parameter chosen from a process input, a setpoint, an alarm, and combinations thereof.

Yet another embodiment of the invention is a linearly scalable 10 liter bioprocessing system which uses the same, or substantially simulates, the polymer chemistry characteristics of each of the components of any one of a 50 liter to a 5000 liter bioprocessing system comprising a flexible-walled bioreactor bag, the 10 liter bioprocessing system comprising: a bioprocessing bag having a working volume of from about 2 liters to about 10 liters; a flexible wall; and an impeller mounted on an impeller plate attached to an inside bottom surface of the flexible wall, the ratio of the diameter of the impeller, Di, to the diameter of the bioprocessing bag, Dt, equal to a value of from about 0.6 to about 0.7, the bioprocessing bag capable of exhibiting substantially the same impeller shear rate and bulk shear rate over a range of values of power per unit volume.

In the linearly scalable 10 liter bioprocessing system described above, which substantially simulates the polymer chemistry characteristics of each of the components of any one of a 50 liter to a 5000 liter bioprocessing system, the bioprocessing bag may comprises polyethylene or alternatively ethylene viny acetate, resin-impregnated fiberglass or carbon fiber, or other polymers such as high-density polyethylene, polyacrylate, polycarbonate, polystyrene, nylon or other polyamides, polyesters, phenolic polymers, and combinations thereof. in the form of a film.

In the linearly scalable 10 liter bioprocessing system which substantially simulates the polymer chemistry characteristics of each of the components of any one of a 50 liter to a 5000 liter bioprocessing system, the bioprocessing bag, the impeller plate, and the impeller may be comprised of the same class of polymers, respectively, as that of the bioprocessing bag, the impeller plate, and the impeller in one of the 50 liter to the 5000 liter bioprocessing systems. Alternatively, the impeller in the disclosed 10 liter bioprocessing system may comprise a material chosen from PEEK™ (Victrex PLC Corp, UK), polycarbonate, stainless steel, resin-impregnated fiberglass, carbon fiber, high-density polyethylene, polyacrylate, polystyrene, a nylon, a polyamide other than nylon, a polyester, a phenolic polymer, and combinations thereof.

The design of the disclosed linearly scalable, bioreactor system, which may be a single-use system, is such that the operating range and geometry of each bioreactor in the system provide the ability to maintain constant shear in each bioreactor.

In one embodiment of the invention, the single-use bioprocessing bag is disposed within a vessel, also referred to herein as a "tank." The vessel may be comprised of a rigid or slightly rigid material and serves to support the bag disposed therein. "Linear scalability," as the term is used herein, refers to the relatively constant value of the H/D ratio at maximum working volume, $V_w$, of the vessel or of the bag disposed therein, and the ability to maintain constant bulk shear, plus or minus 25 percent (+/−25%) across each of the bioreactors in the system for each bioreactor in the system, from 10 L to about 5000 L. A geometric similarity for the vessel or the bag disposed therein, and constant bulk shear are maintained for each bioreactor in the system, across a wide range of working volumes, from about 2 liters to 5000 liters. This linear scalability provides a means to model the performance of a large bioreactor in a smaller bioreactor (scale-down), or conversely for a development process that is carried out in a relatively small bioreactor to be easily scaled up for use in a larger commercial scale process with minimal changes in protocol.

In another aspect, an embodiment of the system provides a 10 L flexible wall bioreactor wherein the product contact surfaces of which the bags and tubing are constructed are the same or are within the same class of polymers for both the small scale, e.g., 4.5 L and 10 L, and the large scale, e.g., 50-5000 L bioreactors. For example, the product contact surface may comprise low density polyethylene (LDPE) or PEEK™, polycarbonate, stainless steel resin-impregnated fiberglass or carbon fiber, or other polymers such as high-density polyethylene, polyacrylate, polystyrene, nylon or other polyamides, polyesters, phenolic polymers, and combinations thereof.

Use of the same class of materials for construction of both large and small bags may be important for scale-up and/or scale-down processing because it avoids or minimizes any potential affect that use of different materials may have on the process.

For example, a 10 L bag of a bioreactor in the disclosed system may comprise the same polymeric film and rigid plastics product contact components as a larger scale bioreactor in the disclosed system. This eliminates the regulatory disconnect between small scale optimization and large scale implementation with respect to extractables and leachables, USP conformance and GMP validation. As a result the 10 L system models larger scale systems, not just from a shear/scalability/performance basis, but also from a validation and regulatory basis. Thus, the linear scalability may also include GMP or cGMP scalability without the necessity of modifying tech transfer.

The design of the disclosed linearly scalable, single-use, 10 L bioreactor system is such that its gas sparging/aeration system is substantially the same as the gas delivery/aeration system of the larger 50-5000 L bioreactor systems, such that the smaller 10 L bioreactor can simulate the performance of the larger systems aeration and gassing performance. This additional feature of linear scalability provides a means to model the performance of a large bioreactor in a smaller bioreactor, or conversely for a development process that is carried out in a relatively small 10 L bioreactor to be easily scaled up for use in a larger commercial scale process with minimal changes in protocol.

In one embodiment of the invention, the single-use bioprocessing bag is disposed within a vessel, also referred to herein as a "tank." The vessel may be comprised of a rigid or slightly rigid material and serves to support the bag disposed therein. In this embodiment, "linear scalability," as the term is used herein, refers to substantially the same gas sparging/aeration components, geometry and porosity as the gas sparging/aeration systems of the 50-5000 L bioreactors systems, with the spargers similarly positioned below the shadow of the rotating impeller blades. This linear scalability allows the bioprocess researcher to simulate the gas transfer rates of larger scale 50-5000 L systems (such as for oxygen supply to and $CO_2$ removal from the cell culture) in the 10 L bioreactor system.

In summary, the 10 L bioreactor system disclosed provides for "linear scalability" by using the same or substantially simulating the same vessel geometry, gas sparging system, impeller shape and type, polymer composition of the flexible bag/components, process control system, and shear rates as used in larger 50 L-5000 L systems. The disclosed 10 L bioreactor system is well suited for mammalian cell, bacterial, plant, insect, protozoan, organ, and/or or fungal cell culture.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Throughout the description and claims of this specification, the words "comprise" and "contain" and variations of these words mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

A linearly scalable, single use, bioreactor system according to an embodiment of the invention is a small-scale bioreactor that provides linear scalability from a small scale, to a large scale, e.g., from a 2 L to a 10 L single-use bioreactor bag to a single 5000 L single-use, bioreactor bag in the same single-use platform within a family of bioreactors of varying sizes.

Figure 1:
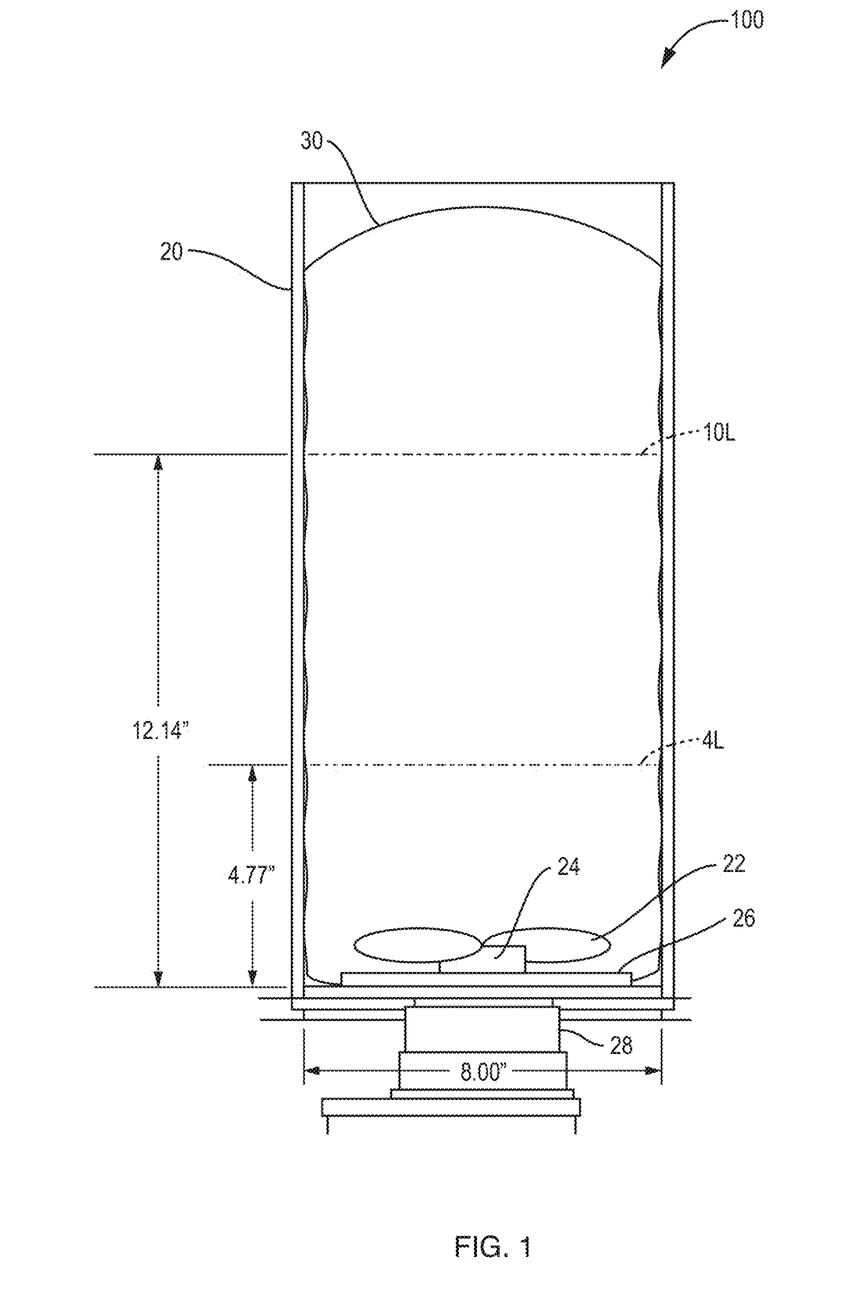
FIG. 1 is a schematic side elevational, cutaway view of a 10 L bioreactor vessel with a single-use, flexible bag disposed therein, an impeller, magnetic impeller hub, impeller plate and, external magnetic drive according to an embodiment if the invention.

FIG. 1 is a schematic side elevational, cutaway view of a disclosed bioreactor system 100 comprising a 10 L bioreactor vessel or support structure 20 with a single-use, flexible bag 30 disposed therein; a 40 degree pitch blade impeller 22 attached to a magnetic hub 24 at the bottom center of the inside of the bag; an impeller plate 26 positioned on the inside bottom of the bag and upon which the magnetic puck 24 rotates; and an external magnetic drive 28. The operating range, in the embodiment depicted in FIG. 1 is from a minimum working volume of about 4.5 L to a maximum working volume of about 10 L. The diameter of the tank Dt is 8 inches. The aspect ratio H/D of height of working volume H to diameter D of the tank is about 1.5 at 10 L working volume and about 0.6 at 4 L working volume. The diameter of the impeller Di is about 5.4 inches. The ratio of Di/Dt is about 6.8. Maximum rpm is about 350. Maximum P/V is 1400 W/m$^3$. There are 4 sintered metal gas sparging discs (not shown) on the impeller plate 26. In an alternative embodiment, drilled holes of from about 0.5 mm to about 1.0 mm can be used for sparging. The bottom spacing or height of the impeller 32 from the impeller plate 26 is about 0.25 times the Di for the 10 L bioreactor bag as shown. The ideal height of the impeller is variable for larger bags, and can be determined with no more than routine experimentation.

A reuseable bioreactor according to the disclosed system may include a reuseable polymeric or metal vessel stand, support, or holder 20 with integral, external motor/agitation assembly 28, and a measurement and control system (not shown). The vessel stand, support, or holder may be comprised of a mixed material such as a polymer with metals. The polymeric or metal vessel can be any shape or size as long as it is capable of supporting the disclosed stirred tank single-use flexible bioreactor bag 30 design. For example, according to one embodiment of the invention a polymeric or metal stand, support, or holder 20 is capable of accepting and supporting a 10 L flexible or collapsible bioprocess bag assembly 30.

Table 1 below shows the scaling factors that were used to produce and configure each of the bioprocessing bags, from 10 liters to 2000 liters represented in Table 2, Table 3A, and Table 3B below.

TABLE 1

| Parameter | XDR 10 | XDR 42.5 | XDR 200 | XDR 500 | XDR 1000 | XDR 2000 |
|---|---|---|---|---|---|---|
| Max. Working Volume (L) | 10 | 42.5 | 200 | 500 | 1000 | 2000 |
| Min. Working Volume (L) | 4.5 | 10 | 40 | 100 | 200 | 400 |
| Tank Diameter (in) | 8 | 12 | 22.5 | 30 | 38 | 48 |
| Max. Liquid height (in) | 12.1 | 17.8 | 33.5 | 45.6 | 56.7 | 70.9 |
| H/D (@max Vw) | 1.5 | 1.5 | 1.5 | 1.5 | 1.5 | 1.5 |
| Impeller diameter (in) | 5.4 | 8.5 | 8.5 | 10.5 | 12.5 | 16.5 |
| Di/Dt | 0.68 | 0.61 | 0.38 | 0.35 | 0.33 | 0.34 |
| Impeller (Pitch Blade) | M40E | M40E | M40E | M40E | M40E | M40E |
| Post orientation | Bot-ctr | Bot-ctr | 15° ba | 15° ba | 15° ba | 15° ba |
| Impeller Np (power #) | 1.50 | 1.50 | 1.15 | 1.15 | 1.15 | 0.72 |
| Impeller to surface (Di's) | 2.2 | 2.5 | 4.2 | 4.6 | 4.7 | 4.4 |
| Sparge orifice (microns)* | 2μ-2 mm | 2μ-2 mm | 2μ-2 mm | 2μ-2 mm | 2μ-2 mm | 2μ-2 mm |

*Sparge flexibility: Sintered and drilled hole sparge options are available. A separate drilled hole sparger is available for $dCO_2$ control as needed.

The measurement and control system is built on a configurable software platform. The measurement and control system operates in real-time; accepts process inputs (measurements) such as temperature, RPM, pH, DO, weight, pressure, etc.; and controls field devices such as mass flow controllers, pumps, solenoid valves, heating elements, and the like. According to one embodiment, human interaction with the system is through a touch-screen based interface that may be on a desk-top, lap-top, or notebook computer, via remote computer operating over the internet, or a remote control device. The interface allows users to enter set-points, manage gas-sparging, calibrate field devices, manage alarms, configure operator identity and access levels, and view process values graphically, over time.

Linear scalability, as described above, is a very important factor especially in the biotech/pharmaceutical manufacturing industry, because it allows easy and simple tech transfer from the research level (small-scale) to the large scale production. As described above, the geometrical similarity, e.g., the aspect ratio (H/D) and type of impeller—are key factors to control and minimize changes in the performance of the bioreactor process during scale up from 2 liters to 5000 liters. As data in the attached Figures, and the Tables below show, a similar H/D aspect ratio for the 2 L to 5000 L scale, the same impeller type and the same gas sparging/aeration components and position for all reactors can help achieve linear scalability and highly predictable scale-up condition modeling, along with maintaining substantially the same bulk shear (+/−25%). Throughout the specification, the 10 L, 42.5 L, 50 L, 200 L, 500 L, 1000 L, and 2000 L single-use bioreactor bags disclosed herein are each designated as the XDR10, XDR42.5, XDR50, XDR200, XDR500, XDR1000, and XDTR2000, respectively.

The data in the above Table 1 show some linear scaling factors for the disclosed single-use bioreactors. Assuming a substantially cylindrical shape throughout the working volume, "Vw" of the single-use bioreactor bag according to an embodiment of the invention, "H" is the height of the working volume in the single-use bag; and "D" is the diameter of the tank or the single use bag, which is disposed within the supporting tank. For a series of maximum working volumes (e.g., 10 L, 200 L, 500 L, 1000 L, and 2000 L), the H/D ratio of either the tank or the bag disposed within is substantially constant, having a value of 1.5. The impeller diameter, "Di," varies, but the impeller type in one embodiment of the invention is a 40 degree pitch blade and is the same type (Model M40E, available from Xcellerex, Inc., Marlborough, Mass., USA) in each system. The number of blades on the impeller may vary. "Np" designates the "power number" of the impeller The impeller in one embodiment is mounted on the impeller plate and is magnetically driven by an external motor. In the XDR10 and XDR42.5, the post is positioned on the center of the inside bottom surface of the bag. In the larger bags, e.g., XDR200 to XDR2000, the post is angled at about 15 degrees off the inside bottom surface of the bag.

The 10 L working volume bag or vessel according to one embodiment of the invention uses the same disposable or single use materials of construction and rigid plastics product contact components as larger scale bioreactors in the same system. The use of the same materials of construction or use of the same class of polymers for construction eliminates the regulatory disconnect between small scale optimization and large scale implementation with respect to extractables and leachables, USP conformance, and validation. As a result, the 10 L system models larger scale systems not just from a shear/scalability/performance basis, but also from a regulatory compliance basis.

Major application areas of a 4 L or a 10 L reactor according to an embodiment of the invention include: a Bench-top bioreactor for research; and a scaled down process optimization tool for any process volumes that are larger than 10 L. The disclosed 4 L or 10 L processing bags can be used for media optimization, clone selection, scale-up testing, including inoculation scale-up study, all of which may be critical to designing large scale upstream operating strategies.

A bioreactor system according to various embodiments of the invention can also be used as an element in a GMP-grade seed train of bioreactors in production/manufacturing. As a seed bioreactor, the disclosed system can be a part of GMP upstream process train.

The disclosed bioreactor system also can include a scale-down system and process from a large bioreactor to a smaller bioreactor, using the same scalability features as the scale-up system. For example, the 4 L and 10 L bags according to an embodiment of the invention can also be used to model the performance of larger systems in "scale-down" experimental processes.

Some of the features of a stirred tank bioreactor in the disclosed system include: a bottom mounted or a side wall-mounted M40E impeller positioned close above substantially the same sparging surface, as described above; USP Class VI materials; full integration with a controller; GMP standard materials in construction; and linear scalability over a wide range of working tank or bag volumes, as described above, for example from 10 L to 2000 L in the same single use bioreactor system.

in the bulk fluid. As such, in a single bioreactor in operation, the bulk shear rate is always lower than the impeller zone shear rate.

Shear rate is the rate at which a shear is applied, and is measured in reciprocal seconds or inverse seconds. The SI unit of measurement for "shear rate" is "s$^{-}$." As used herein, the term "shear" relates in general to a fluid dynamics force or strain on a layer or membrane such as a cell membrane, the strain caused by a fluid moving over the layer or membrane. As stated above, the shear rate is always greater closer to the impeller tip than it is at a greater distance from the impeller tip.

Because each scale-up parameter is dependent on another parameter, all the parameters cannot be kept constant during scale-up. Most commercial bioprocessing scale-up or scale-down protocols hold P/V constant for scaling. However, in the currently available systems, if P/V is constant, the result will be a variable shear rate, which can limit the scalability of the process.

We have now discovered a system comprising two single-use bioreactor bags, each having the same type of impeller; having volumes V1 and V2, wherein V1 is not equal to V2; each bioreactor bag having a working volume height to working volume diameter ratio of approximately 1.5, and wherein the bulk shear rate is substantially the same (+/−25%) for both bioreactors at a given P/V. In one embodiment of the invention the impeller is a pitch blade impeller.

See, for example, the data shown in Tables 2A and 2B below showing that the mixing response at the same P/V across a range of working volumes for single-use bioreactors according to an embodiment of the invention includes a narrow range and approximately constant bulk shear rate.

TABLE 2

| Mixing Response XDR10 L - 2000 L at 6.6 & 25 P/V | | | | | | | | | | | | |
|---|---|---|---|---|---|---|---|---|---|---|---|---|
| XDR | 10 L | 42.5 L | 200 | 500 | 1 KL | 2 KL | 10 L | 42.5 L | 200 | 500 | 1 KL | 2 KL |
| P/V (W/m$^3$) | | | 6.6 | | | | | | 25 | | | |
| rpm | 57 | 47 | 80 | 76 | 73 | 68 | 90 | 73 | 125 | 120 | 113 | 105 |
| Impeller zone shear rate, s$^-$ | 5.5 | 7.0 | 9.4 | 11.0 | 12.6 | 10.8 | 8.6 | 10.9 | 14.7 | 17.4 | 19.5 | 16.7 |
| Bulk shear rate, s$^-$ | 5.4 | 4.4 | 6.6 | 6.3 | 6.1 | 4.7 | 8.5 | 6.9 | 10.4 | 9.9 | 9.4 | 7.2 |
| Eddy scale (μm) | 52 | 48 | 34 | 32 | 30 | 31 | 37 | 35 | 25 | 23 | 22 | 23 |
| KLA (1/h), at 0.01 vvm | 2.0 | 1.3 | 4.4 | 5.8 | 7.0 | 8.5 | 3.5 | 2.0 | 5.9 | 7.9 | 9.4 | 11.4 |
| Vw (L) | 10 | 42.5 | 200 | 500 | 1 KL | 2 KL | 10 | 42.5 | 200 | 500 | 1 KL | 2 KL |

Single Use Bioreactor Scale-Up Factors

As the term is used herein, power input per unit volume (P/V), is the amount of power transferred to a working volume of culture through the rotation of the impeller. The P/V values provided herein have units of 100 watts per cubic meter. As discussed above, mammalian cells have fragile cell membranes that will shear or tear if the P/V is too great. The greatest shear is produced at the tip of the impeller. Therefore, as used herein, the terms "maximum shear rate," "max shear rate," and "impeller zone shear rate," are synonymous and are the shear rate at the tip of the impeller.

As used herein, the term "bulk shear rate" and "average shear rate" are used synonymously are the average shear rate Table 3A below shows, for a given P/V, the bulk shear rate (1/s) for each disclosed embodiment of a single use bioreactor bag from 10 L to 2000 L; the average of the lowest and highest bulk shear rate values, and the maximum percent difference about the average. The median and standard deviation for the range of bulk shear rates are also shown.

Table 3B below shows, for a given P/V, the impeller zone shear rate (1/s) for each disclosed embodiment of a single use bioreactor bag from 10 L to 2000 L; the average of the lowest and highest impeller zone shear rate values, and the maximum percent difference about the average. The median and standard deviation for the range of impeller zone shear rates are also shown.

TABLE 3A

| | Bulk Fluid Shear Rate (1/s) | | | | | | | | | Max Percent Difference about the Average | | | Diff Hi from | Diff Lo from |
|---|---|---|---|---|---|---|---|---|---|---|---|---|---|---|
| P/V (W/m^3) | XDR 10 | XDR 42.5 | XDR 200 | XDR 500 | XDR 1000 | XDR 2000 | Average | Median | Standard Deviation | | High Value | Low Value | Avg | Avg |
| 6.6 | 5.4 | 4.4 | 6.6 | 6.3 | 6.1 | 4.7 | 5.6 | 5.8 | 0.9 | 21 | 6.6 | 4.4 | 1.0 | 1.2 |
| 25 | 8.5 | 6.9 | 10.4 | 9.9 | 9.4 | 7.2 | 8.7 | 9.0 | 1.4 | 21 | 10.4 | 6.9 | 1.7 | 1.8 |
| 100 | 13.7 | 10.9 | 16.6 | 15.9 | | | 14.3 | 14.8 | 2.6 | 24 | 16.6 | 10.9 | 2.3 | 3.4 |

TABLE 3B

| | Impeller Zone Shear Rate (1/s) | | | | | | | | | Max Percent Difference about the Average | | | Diff Hi from | Diff Lo from |
|---|---|---|---|---|---|---|---|---|---|---|---|---|---|---|
| P/V (W/m^3) | XDR 10 | XDR 42.5 | XDR 200 | XDR 500 | XDR 1000 | XDR 2000 | Average | Median | Standard Deviation | | High Value | Low Value | Avg | Avg |
| 6.6 | 5.5 | 7 | 9.4 | 11 | 12.6 | 10.8 | 9.4 | 10.1 | 2.7 | 41 | 12.6 | 5.5 | 3.2 | 3.9 |
| 25 | 8.6 | 10.9 | 14.7 | 17.4 | 19.5 | 16.7 | 14.6 | 15.7 | 4.1 | 41 | 19.5 | 8.6 | 4.9 | 6.0 |
| 100 | 13.8 | 17.3 | 23.4 | 27.8 | | | 20.6 | 20.4 | 6.2 | 35 | 27.8 | 13.8 | 7.2 | 6.8 |

As shown in Table 3A, across a range of single-use bioreactor bags, from about 10 L to about 2000 L, at a given P/V, the bag design provides constant bulk shear rate at a mean value of bulk shear rate +/−24 percent difference between the highest and lowest values.

As shown in Table 3B, the across a range of single-use bioreactor bags, from about 10 L to about 2000 L, at a given P/V, the bag design provides impeller zone shear rates with a maximum percent difference about the average of the highest and lowest values of 41 percent.

Successful scale-up (SU) and/or scale-down (SD) of biologics production requires that performance equivalence be achieved between scales of operation. The SU and SD platform design of the disclosed scalable, single-use 10 L bioreactor design provide a unique system for accomplishing this. The most commonly used SU basis for stirred tank reactor (STR) designs like the disclosed 10 L bioreactor bag design is one that maintains an equal process power input per unit volume of culture fluid, i.e. "constant P/v" (Ref. 1). The wide acceptance of this SU basis in the cell culture industry is the fact that P/V is one of the primary variables that drive the Mass Transfer (MT) demand of the Process, or oxygen uptake rate (OUR).

While achieving the required process OUR, it is also desirable that the physical shear in the SU or SD platform operate within the acceptable shear limits established for the process. The shear rate has been proven a reliable metric for cell culture. The maximum shear rate, that occurs at the impeller tip depends on the impeller diameter, the impeller speed, and the impeller design. The average shear rate in the bulk fluid depends on impeller speed, and impeller design (Ref. 2). The impeller design factors are measured values (Ref. 3), and can be estimated based on the impeller blade angle and solidity. It is common to find a wide range of impeller shear rates and. bulk shear rates in available SU and SD platforms.

Figure 2:
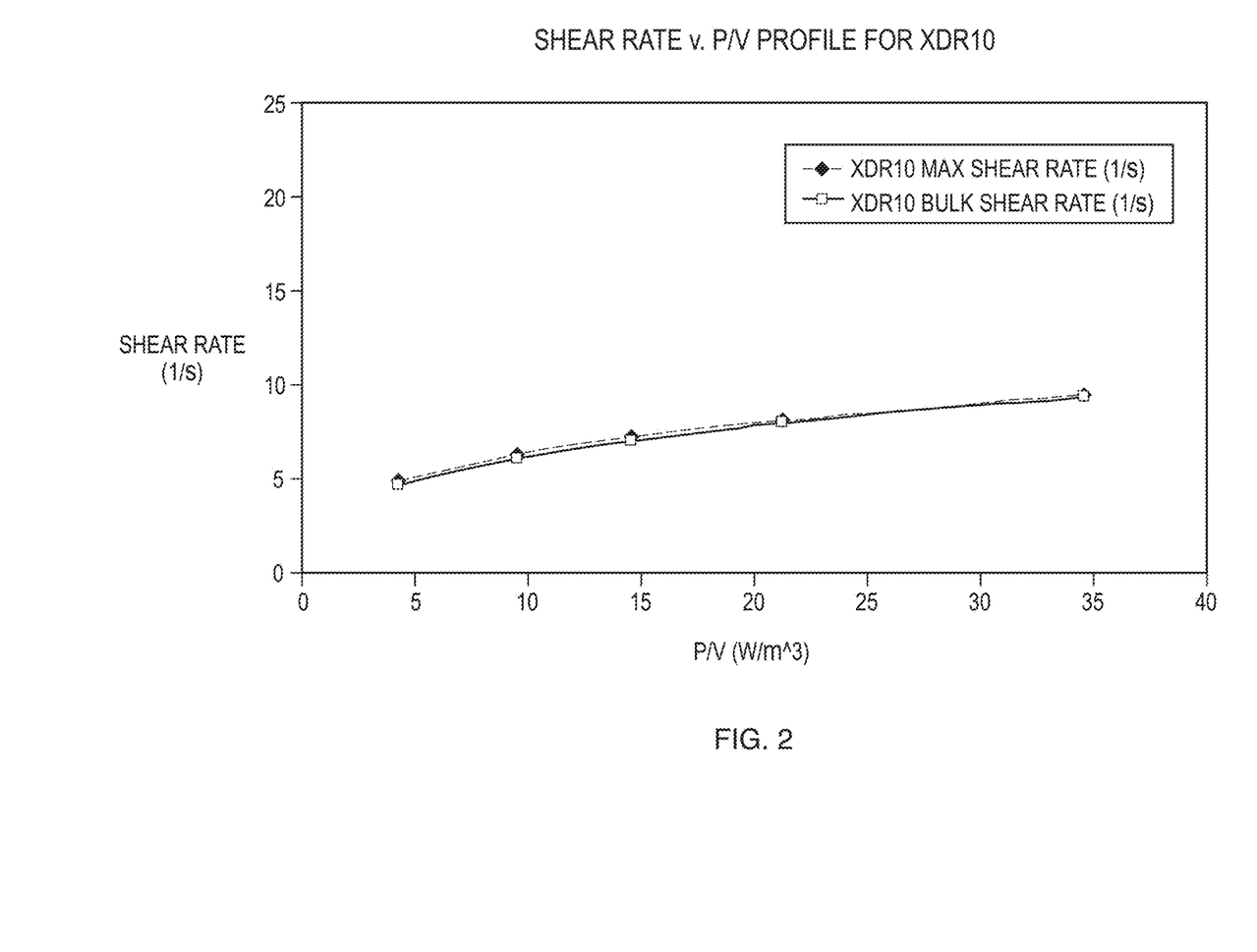
FIG. 2 shows a graphical representation of bulk or average shear rate (unshaded squares) versus power per unit working volume for the 10 L flexible bag bioreactor system; and maximum shear rate at the tip of the impeller (shaded diamonds) versus power per unit working volume for the 10 L flexible bioprocessing bag or bioreactor bag.

As shown in the graph of FIG. 2, the unique, disclosed 10 L design results in nearly equivalent max and bulk shear rates, that is, a uniform shear rate profile, for a range of P/V and rpm needed for cell culture processes. The uniformity in shear profile in the disclosed 10 L will provide an advantage when used as a SD or SU platform.

For the disclosed 10 L single-use bioreactor bag, as shown in FIG. 2, there is a surprising or unexpected uniformity of bulk shear rate and impeller shear rate across a broad range of P/V. It has also been discovered that the disclosed 10 L single-use bioreactor bag impeller zone shear rate is less than the impeller zone shear rate of any larger scale bioreactor system at the same P/V.

According to an embodiment of the disclosed system, the working volume range for a vessel or a bag disposed within the vessel may be from about 10 milliliters (ml) to about 50 milliliters (ml), or from about 50 ml to about 100 ml, or from about 100 ml to about 10 liters (L), Typical working volumes for vessels and bags in bioreactors in the disclosed system may be about 4.5 L, 10 L, 50 L, 200 L, 500 L, 1000 L, 2000 L, and 5000 L. Constant bulk shear rate may be maintained in each of these volumes. For a given disposable bioreactor bag, the bulk shear rate for an impeller can be calculated at low and at high revolutions per minute (rpm). A controller for the system can be utilized for selecting a bulk shear rate, which can be dialed in to change the rpm of the variable speed impeller. The same power per working volume (P/V) can be maintained in a smaller bag, e.g., a 10 liter bag, as in a larger reactor bag, without incurring, within +/−25%, a higher bulk shear rate. High bulk shear rate and/or high maximum shear rate are/is deleterious to mammalian cells.

Fittings are added to the bag to enable functionality required in a bioreactor such as penetrations and filters to allow for fluid and gas transfer, a mixing interface, sensors and a sparging surface to control bubble size. Multiple sparging surfaces and options can be utilized in various embodiments of the invention. A sparging surface can be attached to the bioprocessing bag as an adapter or a bulkhead fitting, designed to connect a hose or tubing such as an oxygen supply tubing to the bag. The porosity and the area of a sparge surface can vary. In one embodiment, a sparging surface may be simply a single hole or a plurality of holes configured to add oxygen gas or air to the bioreactor bag. The sparging surface may be positioned under the impeller to allow for efficient circulation of gas through the media in the bag and its position and type is substantially the same as the position and type in the larger 50 L-5000 L systems.

In another aspect, an embodiment of the disclosed system comprises a single-use bioprocessing bag wherein the distance of the impeller from the sparging surface in each bag of the system is maintained at less than the diameter of the impeller. Minimizing the gap between the impeller and the sparging surface provides for an efficient rate of gas bubbling and oxygen transfer. Positioning the impeller over and close to a sparge surface results in a high value for the volumetric oxygen transfer coefficient, KLa, even for a low volume bag. In one embodiment of the invention the gap between the impeller and the sparging surface is maintained at from about 3 millimeters (mm) to about 200 millimeters (mm), or from about 6 millimeters to about 100 millimeters. In one embodiment the impeller-sparging gap is about 6.25 mm, and its position and type is substantially the same as in the larger 50-5000 L systems.

The linearly scalable bioreactor system according to an embodiment of the invention may include a temperature controller and at least one sensor and/or a probe (not shown). To eliminate utilities required for temperature control through a heat exchanger, heating can be provided by means of closed loop water jacket heated and/or cooled by control system mounted on the bioprocessing bag or by an electric heating blanket(s), or a Peltier heater. The heat blanket may include a thermocouple(s) for sensing a temperature of the contents of the bioprocessing bag, working in conjunction with the temperature controller to control a set temperature of the contents of the bioprocessing bag. A temperature conducting material may be embedded in the surface of the bioprocessing bag to counteract the insulating effect of plastic if necessary.

Cooling may also be provided by a closed loop water jacket heated and/or cooled by control system mounted on the bioprocessing bag or by standard heat exchange through a cover or jacket on the tank supporting the bioprocessing bag. Cooling may also be provided by means of Peltier coolers. For example, a Peltier cooler may be applied to an exhaust line (e.g., to a chamber similar to a small bag, with a large volume to decelerate air and a large surface area situated in a heat exchanger) to condense gas in the exhaust air to help prevent an exhaust filter from wetting out. Alternatively, the exhaust filter may be heated by a filter heater to help prevent condensation of moisture from the exhaust line.

The bioprocessing bag, including all attachments, penetrations, sensors, etc,) may be sterilized prior to use (e.g., gamma-irradiation). After sterilization, the inside of the bag, tubing and components may be considered sterile, providing a "sterile envelope" protecting the contents of the vessel from airborne contaminants outside.

It should also be appreciated that there are at least three basic modes of operation used by stirred tank bioreactors, and that the disclosed bioreactor system comprises bioreactors that can be easily modified to operate in any of the three modes. The three modes are as follows.

Semi-continuous, Continuous or Perfusion Mode: In a semi-continuous, continuous or perfusion mode, nutrients and supporting process fluids are continuously added to the system; waste products are continuously removed either continuously of periodically ("drain and fill"); and product is harvested intermittently or throughout the culture period. With the continuous mode, the on-going difficulty in obtaining sufficiently high product titers is well recognized. In addition to the low titers, there is a need to concentrate product of the continuous mode.

Batch Mode: In batch mode, all nutrients are added at the beginning and products are not removed until the end of the batch. Waste products accumulate during the run, and nutrients are used up, making the batch process inefficient for many applications.

Fed-Batch Mode: A fed-batch mode is similar to the batch mode in that products are removed only at the end of the run, but differs in that nutrients are added at multiple intervals during the process. Many biotherapeutics and most virus-producing, microcarrier cultures are carried out, post infection, in a fed-batch process.

REFERENCES

Ref. 1. Edward L. Paul (ed); *Handbook of Industrial Mixing*, John Wiley & Sons (pub), p 1077 (2003).

Ref. 2. Nelson, K L, (ed); *BioProcess Engineering: Systems*, John Wiley & Sons (pub), (1994), Chapter 1 (Bioreactor design), P 23.

Ref. 3. Beenackers, ACM, et al, *Biochemical Engineering Journal*, 6 (2000) 109-144; p 112.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims and abstract), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims and abstract), or to any novel one, or any novel combination, of the steps of any method or process so disclosed.

What is claimed is:

1. A linearly scalable bioreactor system for use in carrying out a scalable biomanufacturing process, the system comprising:

a first bioprocessing bag having a flexible wall, a working volume of from about 2 liters to about 10 liters, a height to diameter ratio at maximum working volume of about 1.5, and an impeller mounted on an impeller plate attached to an inside bottom surface of the flexible wall, the ratio of the diameter of the impeller, Di, to the diameter of the first bioprocessing bag, Dt, equal to a value of from about 0.6 to about 0.7, the first bioprocessing bag being capable of exhibiting substantially the same impeller shear rate and bulk shear rate over a range of values of power per unit volume, wherein the range of values of power per unit volume is from about 2 Watts per cubic meter to about 36 Watts per cubic meter; and a second bioprocessing bag having a second flexible wall, a second working volume of from about 50 liters to about 5000 liters, a height to diameter ratio at maximum working volume of about 1.5, and a second impeller mounted on a second impeller plate attached to an inside bottom surface of the second flexible wall, the ratio of the diameter of the second impeller, D2$i$, to the diameter of the second bioprocessing bag, D2$t$, not being equal to a value of from about 0.6 to about 0.7, the second bioprocessing bag being capable of exhibiting substantially the same impeller shear rate and bulk shear rate over a range of values of power per unit volume;

wherein the impeller of the first bioprocessing bag and the impeller of the second bioprocessing bag are of the same type;

wherein at a power per unit volume of about 6.6 Watts per cubic meter, the first bioprocessing bag exhibits a bulk shear rate of about 5.4 and the second bioprocessing bag exhibits a bulk shear rate within about +/−25 percent of the bulk shear rate exhibited by the first bioprocessing bag; and wherein the first bioprocessing bag and the second bioprocessing bag provide for linear scalability of a biomanufacturing process from the first bioprocessing bag to the second bioprocessing bag.

2. The linearly scalable bioreactor system of claim 1, wherein the maximum working volume of the first bioprocessing bag is about 10 liters.

3. The linearly scalable bioreactor system of claim 1, wherein:

the first bioprocessing bag has a working volume of about 2 liters.

4. The linearly scalable bioreactor system of claim 1, wherein the maximum shear rate or the impeller shear rate of the first bioprocessing bag in operation is less than the maximum shear rate or the impeller shear rate of any larger scale bioprocessing system operating at the same power per unit volume.

5. The linearly scalable bioreactor system of claim 1, wherein the flexible wall of the first bioprocessing bag comprises polyethylene.

6. The linearly scalable bioreactor system of claim 1, wherein the impeller of the first bioprocessing bag is a pitch blade impeller mounted on the center of the impeller plate.

7. The linearly scalable bioreactor system of claim 1, comprising a sparging surface positioned beneath the impeller of the first bioprocessing bag.

8. The linearly scalable bioreactor system of claim 1, comprising a sensor.

9. The linearly scalable bioreactor system of claim 1, comprising a means for heating or cooling contents of the first bioprocessing bag.

10. The linearly scalable bioreactor system of claim 1, comprising a means for collecting and condensing the exit air gas, followed by filtration of the gas.

11. The linearly scalable bioreactor system of claim 1, comprising a measurement and control system including a configurable software platform, the control system capable of operating in real-time and capable of accepting measurement inputs and controlling at least one component of the bioreactor system.

12. The linearly scalable bioreactor system of claim 11, comprising a means for human interaction with the system through a touch-screen based interface on a device chosen from a desk-top computer, a lap-top computer, a notebook computer, and a remote control device.

13. The linearly scalable bioreactor system of claim 12, wherein the touch-screen based interface is configured for allowing a user to enter set-points, calibrate field devices, manage alarms, configure operator identity and access levels, and view process values graphically, over time.

* * * * *